United States Patent
Israelsson et al.

(10) Patent No.: US 6,736,805 B2
(45) Date of Patent: *May 18, 2004

(54) HYDROPHILIC URINARY CATHETER HAVING A WATER-CONTAINING SACHET

(75) Inventors: Anette Israelsson, Göteborg (SE); Agneta Pettersson, Göteborg (SE); Jan Utas, Kungsbacka (SE)

(73) Assignee: AstraZeneca AB, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 10/160,390

(22) Filed: May 31, 2002

(65) Prior Publication Data

US 2002/0156440 A1 Oct. 24, 2002

Related U.S. Application Data

(63) Continuation of application No. 08/809,481, filed as application No. PCT/SE97/00096 on Jan. 22, 1997, now Pat. No. 6,409,717.

(30) Foreign Application Priority Data

Jan. 25, 1996 (SE) ................................. 9600276

(51) Int. Cl.⁷ .............................................. A61M 27/00
(52) U.S. Cl. ........................ 604/544; 604/317; 604/540; 206/571; 206/363; 206/364
(58) Field of Search ................................. 604/172, 265, 604/349, 262, 523, 544, 264, 317, 328; 206/438, 571, 363, 364

(56) References Cited

U.S. PATENT DOCUMENTS

| | | | |
|---|---|---|---|
| 1,120,549 A | 12/1914 | Schellberg | |
| 2,856,932 A | 10/1958 | Griffitts | 604/171 |
| 2,872,433 A | 4/1959 | Glickman | 260/45.7 |
| 3,005,728 A | 10/1961 | Bridgeford | 117/118 |
| 3,023,126 A | 2/1962 | Underwood et al. | 117/76 |
| 3,035,691 A | 5/1962 | Rasmussen et al. | 206/63.2 |
| 3,064,800 A | 11/1962 | Hart | 206/42 |
| 3,169,527 A | 2/1965 | Sheridan | 128/349 |
| 3,198,692 A | 8/1965 | Bridgeford | 161/188 |
| 3,216,983 A | 11/1965 | Shelanski et al. | 260/88.3 |
| 3,345,988 A | 10/1967 | Vitello | 128/349 |
| 3,403,766 A | 10/1968 | Mason | 197/107 |
| 3,421,509 A | 1/1969 | Fiore | 128/349 |

(List continued on next page.)

FOREIGN PATENT DOCUMENTS

| | | |
|---|---|---|
| GB | 2284764 | 6/1995 |
| JP | 5550370 | 4/1980 |
| JP | 61501750 | 8/1986 |
| WO | 8606284 | 11/1986 |

*Primary Examiner*—Weilun Lo
*Assistant Examiner*—Michele Kidwell
(74) *Attorney, Agent, or Firm*—Fish & Neave; Jeffrey H. Ingerman

(57) ABSTRACT

A wetting apparatus (110) for wetting a hydrophilic urinary catheter (103) comprises a wetting receptacle (101) which defines a wetting fluid receiving area (102) for receiving the hydrophilic urinary catheter and a hydrophilic urinary catheter wetting fluid container (106) having a discharge outlet (126) movable from a closed position to an open position on application of a predetermined condition thereto to enable the wetting fluid to be discharged from the wetting fluid container. The wetting fluid container provided can be positioned in the wetting receptacle in an operational position in which at least the discharge outlet of the wetting fluid container is disposed within the bounds of the wetting receptacle, the wetting receptacle being so constructed and the wetting fluid container being so disposed relative to the wetting receptacle when in the operational position that application of the predetermined condition to the discharge outlet of the wetting fluid container when in the operational position enables the wetting fluid to be discharged into the wetting fluid receiving area for wetting of the hydrophilic urinary catheter.

26 Claims, 4 Drawing Sheets

U.S. PATENT DOCUMENTS

| | | | |
|---|---|---|---|
| 3,444,860 A | 5/1969 | Harrell | 128/349 |
| 3,556,294 A | 1/1971 | Walck, III et al. | 206/63.2 |
| 3,566,874 A | 3/1971 | Shepherd | 128/349 |
| 3,648,704 A | 3/1972 | Jackson | 604/172 |
| 3,661,634 A | 5/1972 | Riley et al. | 117/161 |
| 3,674,195 A | 7/1972 | Stone | 229/66 |
| 3,730,337 A | 5/1973 | White | 206/47 |
| 3,794,042 A | 2/1974 | De Klotz et al. | 128/349 |
| 3,861,395 A | 1/1975 | Taniguchi | 128/349 |
| 3,886,947 A | 6/1975 | Sawyer | 128/348 |
| 3,895,169 A | 7/1975 | Wichterle | 428/420 |
| 3,898,993 A | 8/1975 | Taniguchi | 128/349 |
| 3,926,309 A | 12/1975 | Center | 206/364 |
| 3,934,721 A | 1/1976 | Juster et al. | 206/364 |
| 3,954,174 A | 5/1976 | Kraus | 206/223 |
| 3,958,750 A | 5/1976 | Prybeck | 229/56 |
| 3,967,728 A | 7/1976 | Gordon et al. | 206/364 |
| 3,975,350 A | 8/1976 | Hudgin et al. | 260/30.4 |
| 4,053,696 A | 10/1977 | Herrle et al. | 526/65 |
| 4,091,922 A | 5/1978 | Egler | 206/364 |
| 4,094,967 A | 6/1978 | Gilbert | 424/28 |
| 4,100,309 A | 7/1978 | Micklus et al. | 427/2 |
| 4,119,094 A | 10/1978 | Micklus et al. | 128/132 |
| 4,128,600 A | 12/1978 | Skinner et al. | 260/859 |
| 4,143,423 A | 3/1979 | Sternlieb | 2/168 |
| 4,154,244 A | 5/1979 | Becker et al. | 128/349 |
| 4,188,954 A | 2/1980 | Patel et al. | 128/349 |
| 4,230,115 A | 10/1980 | Walz, Jr. et al. | 128/295 |
| 4,232,608 A | 11/1980 | Wrightson | 102/103 |
| 4,269,310 A | 5/1981 | Uson | 206/210 |
| 4,318,947 A | 3/1982 | Joung | 428/36 |
| 4,366,901 A | 1/1983 | Short | 206/210 |
| 4,373,009 A | 2/1983 | Winn | 428/424.2 |
| 4,379,506 A | 4/1983 | Davidson | 206/364 |
| 4,417,612 A | 11/1983 | Couture et al. | 150/40 |
| 4,459,317 A | 7/1984 | Lambert | 427/2 |
| 4,481,323 A | 11/1984 | Sterling | 524/269 |
| 4,515,593 A | 5/1985 | Norton | 604/265 |
| 4,526,579 A | 7/1985 | Ainpour | 604/265 |
| 4,585,666 A | 4/1986 | Lambert | 427/2 |
| 4,589,873 A | 5/1986 | Schwartz et al. | 604/265 |
| 4,597,765 A | 7/1986 | Klatt | 623/11 |
| 4,652,259 A | 3/1987 | O'Neil | 604/54 |
| 4,666,437 A | 5/1987 | Lambert | 604/265 |
| 4,677,143 A | 6/1987 | Laurin et al. | 523/122 |
| 4,692,154 A | 9/1987 | Singery et al. | 604/172 |
| 4,754,877 A | 7/1988 | Johansson et al. | 206/364 |
| 4,769,013 A | 9/1988 | Lorenz et al. | 604/265 |
| 4,772,275 A | 9/1988 | Erlich | 604/280 |
| 4,773,901 A | 9/1988 | Norton | 604/265 |
| 4,811,847 A | 3/1989 | Reif et al. | 206/571 |
| 4,842,597 A | 6/1989 | Brook | 604/368 |
| 4,863,442 A | 9/1989 | DeMello et al. | 604/282 |
| 4,898,591 A | 2/1990 | Jang et al. | 604/282 |
| 4,906,237 A | 3/1990 | Johansson et al. | 604/265 |
| 4,921,483 A | 5/1990 | Wijay et al. | 604/96 |
| 4,928,830 A | 5/1990 | Brewer | 206/570 |
| 5,091,205 A | 2/1992 | Fan | 427/2 |
| 5,094,876 A | 3/1992 | Goldberg et al. | 427/2 |
| 5,105,942 A | 4/1992 | van Veen et al. | 206/364 |
| 5,125,416 A | 6/1992 | Phillips | 128/772 |
| 5,147,341 A | 9/1992 | Starke et al. | 604/349 |
| 5,160,559 A | 11/1992 | Scovil et al. | 156/73.6 |
| 5,160,790 A | 11/1992 | Elton | 428/412 |
| 5,209,726 A | 5/1993 | Goosen | 604/349 |
| 5,217,493 A | 6/1993 | Raad et al. | 623/11 |
| 5,226,530 A | 7/1993 | Golden | 206/210 |
| 5,242,428 A | 9/1993 | Palestrant | 604/265 |
| 5,322,163 A | 6/1994 | Foos | 206/364 |
| 5,342,386 A | 8/1994 | Trotta | 606/194 |
| 5,385,152 A | 1/1995 | Abele et al. | 128/772 |
| 5,416,131 A | 5/1995 | Wolff et al. | 523/105 |
| 5,433,713 A | 7/1995 | Trotta | 604/264 |
| 5,454,798 A | 10/1995 | Kubalak et al. | 604/328 |
| 5,738,213 A | 4/1998 | Whiting et al. | 206/364 |
| 5,756,144 A | 5/1998 | Wolff et al. | 427/2.3 |
| 5,776,611 A | 7/1998 | Elton et al. | 428/423.1 |
| 5,849,843 A | 12/1998 | Laurin et al. | 525/66 |
| 5,853,518 A | 12/1998 | Utas | 156/245 |
| 6,065,597 A | 5/2000 | Pettersson et al. | 206/364 |
| 6,409,717 B1 * | 6/2002 | Israelsson et al. | 604/544 |

\* cited by examiner

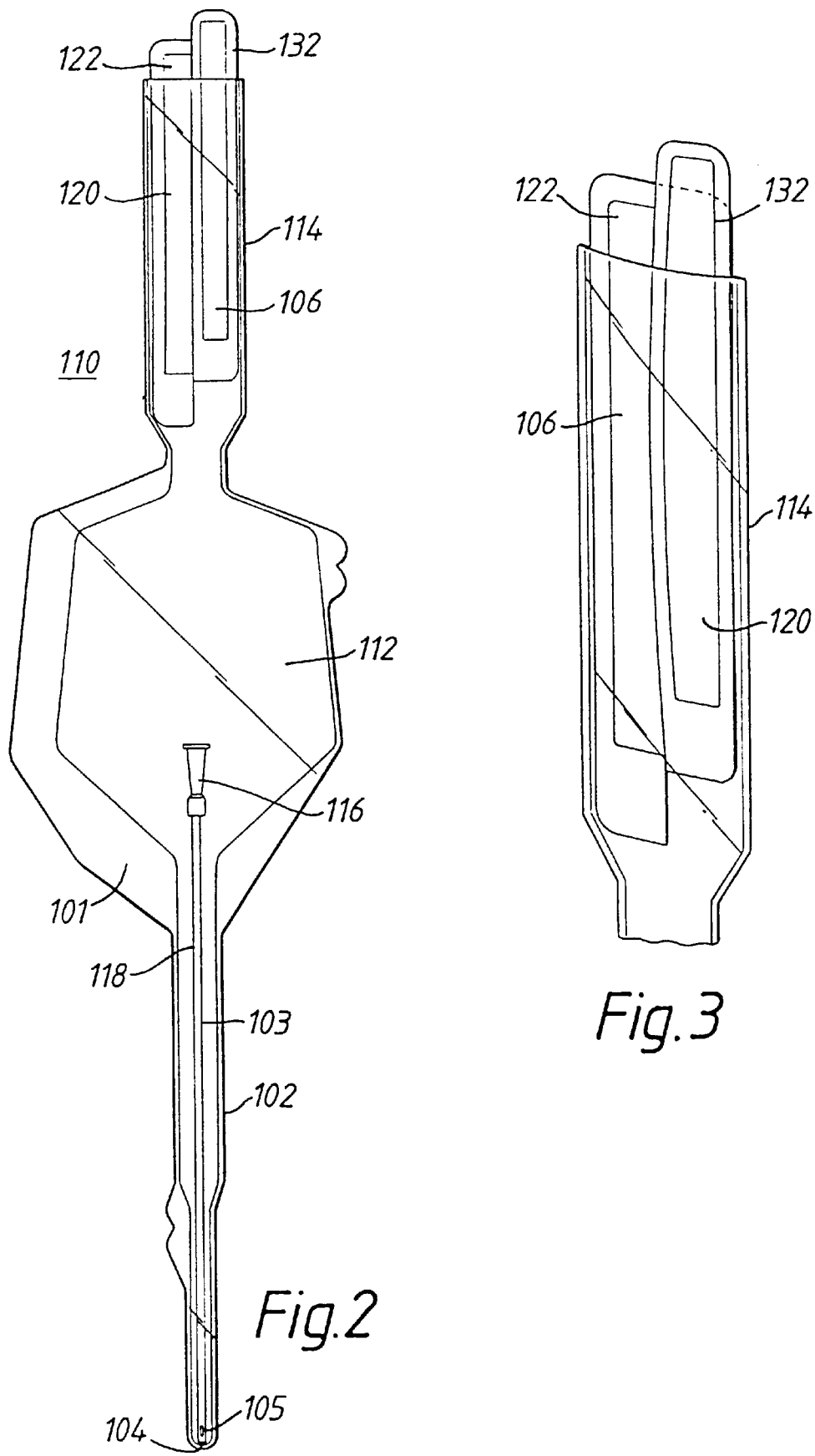

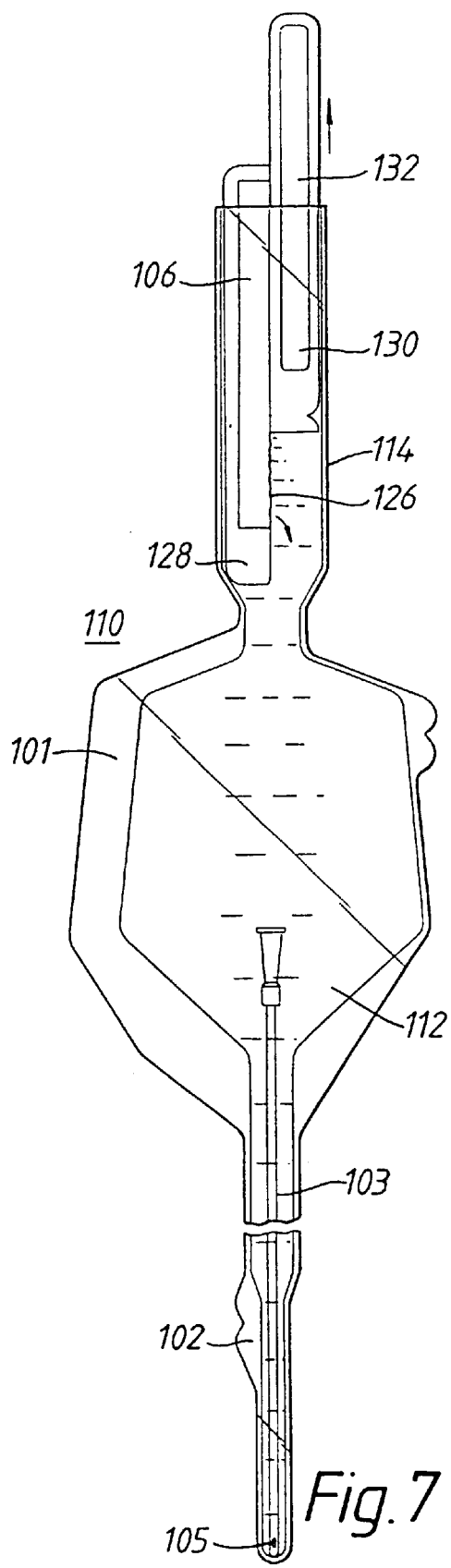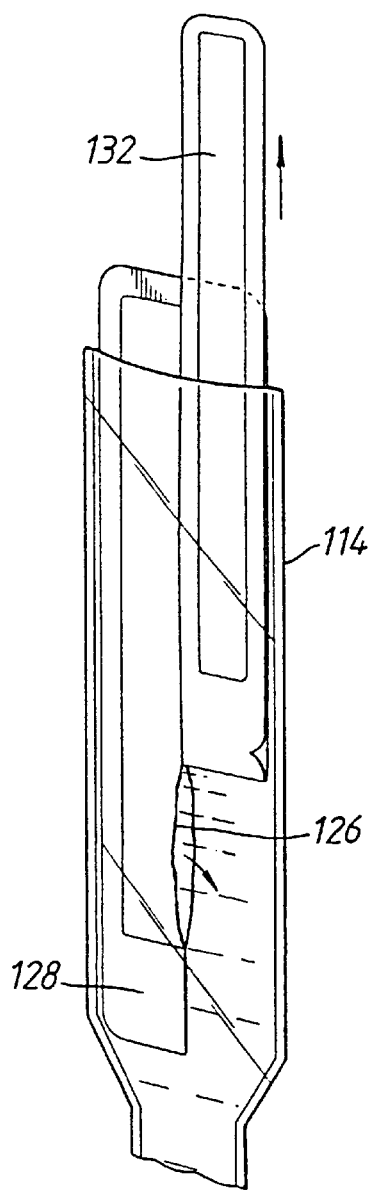

HYDROPHILIC URINARY CATHETER HAVING A WATER-CONTAINING SACHET

This application is a continuation Application under 37 of U.S. Application Ser. No. 08/809,481, filed Mar. 21, 1997 now U.S. Pat. No. 6,409,717, which was the U.S. National Stage filing of International Application No. PCT/SE97/00096, filed Jan. 22, 1997.

BACKGROUND OF THE INVENTION

The present invention relates to wetting apparatus for wetting of hydrophilic urinary catheters comprising a wetting receptacle which defines a wetting fluid receiving area which is adapted to receive a hydrophilic urinary catheter and a hydrophilic urinary catheter wetting fluid container having a discharge outlet movable from a closed position to an open position on application of a predetermined condition thereto to enable the wetting fluid to be discharged from the wetting fluid container into the wetting fluid receiving area for wetting of the hydrophilic urinary catheter. The present invention further relates to a fluid container of a type which may be used in such apparatus.

Intermittent self-catheterisation is widely employed by patients suffering from for example strictures or traumas in the urinary system as well as by paralysed patients to enable the patients to live a nearly normal home life. Urinary catheters supplied for intermittent self-catheterisation in general need to have a lubricant applied to the outer surfaces thereof to facilitate insertion into the urethra. For example, hydrophilic urinary catheters have a hydrophilic outer surface coating which should be wetted by a fluid such as water or saline for a certain time period prior to insertion thereof into the urethra of a patient for lubrication purposes.

Various methods for lubricating urinary catheters have been previously proposed, examples of which are given below.

Prior U.S. Pat. No. 5,209,726 makes known a self-lubricating urinary catheter and a method for self-catherisation. The catheter has an annular lubricant reservoir surrounding an inner tube having perforations. As the catheter is inserted into the urethra of a patient lubricant is forced from the reservoir into the inner tube and out into the urethra through a discharge outlet in the catheter. Lubrication of the outer surface of the catheter therefore only takes place as the catheter is being inserted into the urethra of the patient resulting in at least some initial discomfort for the patient on insertion of the catheter.

Prior U.S. Pat. No. 3,967,728 makes known a catheter package comprising a urinary catheter and a rupturable, lubricant containing pouch. One edge of the pouch is located within the package adjacent to the tip of the catheter and the seal at that edge is made so that it ruptures when the pouch is squeezed thereby to lubricate the tip of the catheter. As only the tip of the catheter is lubricated the patient will still suffer discomfort on insertion of the catheter into the urethra.

Prior UK patent application publication No. 2284764 makes known a catheter and urine collection bag assembly comprising (i) a catheter having a shaft with a rounded tip, a drainage aperture in the tip and a flared portion to the rear of the shaft, and (ii) a urine collection bag within which the catheter is disposed and which at a forward end is formable with an aperture which is sufficiently large to permit the tip and shaft of the catheter to pass through but small enough for the flared portion of the catheter to engage therewith to form a mechanical seal against leakage of urine. Once the catheter has been extended through the aperture it is ready to be inserted into the urethra of a patient. Urine is transported rearwardly through the catheter from the bladder of the patient for collection in the urine collection bag. It is disclosed that a separate, burstable container containing a lubricious substance may be included within the urine collection bag for lubricating the catheter. No details are given, however, of the construction of the container nor of the disposition of the container relative to the catheter.

Applicant's prior International patent application publication No. WO86/06284 discloses a wetting and storage device for a hydrophilic urinary catheter. A wetting pocket is provided, closed at one end so that it may be filled with a wetting liquid and a hydrophilic urinary catheter is then introduced into the pocket for wetting thereof. No liquid container, though, is provided in the device for releasing wetting liquid into the pocket immediately prior to use of the catheter. Wetting liquid for the pocket therefore has to be supplied separately by the patient. This is inconvenient because a sterile supply of wetting liquid is not necessarily always on hand to the patient and there is a marked possibility of spillage of the wetting liquid.

The hitherto proposed lubricating apparatus for urinary catheters discussed above have the drawback that they make no or inadequate provision for lubricating hydrophilic urinary catheters. As an example, the lubricating arrangements made known in U.S. Pat. No. 3,967,728 and UK patent application publication No. 2284764 are for catheters of non-hydrophilic character, the lubricant therefore being a gel which is unsuited for lubricating a hydrophilic catheter. The prior lubricating apparatus therefore fail to provide an integrated supply of hydrophilic urinary catheter wetting fluid let alone an integrated supply of hydrophilic urinary catheter wetting fluid which on discharge results in wetting of the insertable length or substantially the insertable length of a hydrophilic urinary catheter prior to insertion of the catheter into the urethra of a patient.

Patients using hydrophilic urinary catheters accordingly require improved means for lubricating the catheters. The present invention therefore proposes to address this requirement.

SUMMARY OF INVENTION

According to a first aspect of the invention there is provided a wetting apparatus for wetting a hydrophilic urinary catheter comprising a wetting receptacle which defines a wetting fluid receiving area for receiving a hydrophilic urinary catheter and a hydrophilic urinary catheter wetting fluid container having a discharge outlet movable from a closed position to an open position on application of a predetermined condition thereto to enable the wetting fluid to be discharged from the wetting fluid container, the wetting fluid container being integrated with the wetting receptacle in an operational position in which at least the discharge outlet of the wetting fluid container is disposed within the bounds of the wetting receptacle, the wetting receptacle being so constructed and the wetting fluid container being so disposed relative to the wetting receptacle when in the operational position that application of the predetermined condition to the discharge outlet of the wetting fluid container when in the operational position enables the wetting fluid to be discharged into the wetting fluid receiving area for wetting of the hydrophilic urinary catheter and the wetting fluid receiving area being adapted such that the insertable length or substantially the insertable length of the hydrophilic urinary catheter is wetted by the wetting fluid discharged into the wetting fluid receiving area.

By "integrated" is meant that the wetting fluid container and wetting receptacle are formed into a one-piece unit, that is to say, the wetting fluid container is supported on or by the wetting receptacle.

An "on tap" supply of lubricant for the hydrophilic urinary catheter is therefore available to the patient and the problem of possible spillage of the wetting fluid alleviated. Furthermore, an increased comfort on insertion of the catheter into the urethra results due to the insertable length or substantially the insertable length of the catheter being lubricated prior to insertion.

According to a second aspect of the invention there is provided a wetting apparatus for wetting a hydrophilic urinary catheter comprising a wetting receptacle which defines a wetting fluid receiving area for receiving a hydrophilic urinary catheter and a hydrophilic urinary catheter wetting fluid container having a discharge outlet movable from a closed position to an open position on application of a predetermined condition thereto to enable the wetting fluid to be discharged from the wetting fluid container, the wetting fluid container being integrable with the wetting receptacle in an operational position in which at least the discharge outlet of the wetting fluid container is disposed within the bounds of the wetting receptacle, the wetting receptacle being so constructed and the wetting fluid container being so disposed relative to the wetting receptacle when in the operational position that application of the predetermined condition to the discharge outlet of the wetting fluid container when in the operational position enables the wetting fluid to be discharged into the wetting fluid receiving area for wetting of the hydrophilic urinary catheter. The problem of possible spillage of the wetting fluid is also alleviated in this case and manufacture, packaging and transport of the apparatus simplified.

In a preferred embodiment of the invention the wetting fluid is water or a saline solution.

In an embodiment of the invention hereinafter to be described the wetting fluid receiving area is an elongate pocket of length sufficient to accommodate at least the insertable length of the hydrophilic urinary catheter and the wetting fluid container is adapted to contain sufficient wetting fluid to fill the pocket to a level for wetting at least the insertable length of the hydrophilic urinary catheter.

In a preferred embodiment of the invention hereinafter to be described the wetting receptacle is a urine collection bag, the elongate pocket forms the forward portion of the urine collection bag and presents an open rear end and a weakened closed forward end which is removable upon application of a predetermined pressure thereto thereby to enable a portion of the hydrophilic urinary catheter comprising at least the insertable length thereof to be projected through the forward end of the pocket after wetting thereof for insertion into the urethra of a patient and the urine collection bag further comprises a urine collection chamber to the rear of the elongate pocket, the urine collection chamber having a forward end which is in fluid communication with the open rear end of the pocket and being adapted in use to collect urine transported rearwardly through the hydrophilic urinary catheter after insertion thereof into the urethra of the patient.

A typical sterilising agent which could be used for sterilising the wetting apparatus of the invention is ethylene oxide. Moreover, the fluid in the fluid container would normally be sterile. For these reasons, the wetting fluid container is preferably made of a material which is impermeable or substantially impermeable to ethylene oxide as well as the fluid contained therein. Non-limiting examples of materials satisfying this condition when the fluid is water or saline are aluminium foil, poly(vinylidene chloride) or a metallised film such as metallised poly(ethylene terepthalate).

In an embodiment of the invention hereinafter to be described the wetting fluid container is fully contained within the bounds of the wetting receptacle and may be permanently fixed to the inner surface of the wetting receptacle.

In an embodiment of the invention the wetting fluid container is an integrally formed compartment of the wetting receptacle.

In an embodiment of the invention hereinafter to be described the wetting receptacle is formed of a flexible material and the discharge outlet is brought to the open position through application of a predetermined force to the wetting fluid container through the material of the wetting receptacle.

In an embodiment of the invention hereinafter to be described the wetting receptacle is provided with an inlet which is in fluid communication with the wetting fluid receiving area and the wetting fluid container is integrable with the wetting receptacle in the operational position by insertion of at least a forward portion thereof in the inlet, the forward portion of the wetting fluid container presenting the discharge outlet.

In an embodiment of the invention hereinafter to be described the wetting fluid container is integrable with the wetting receptacle in the operational position through a friction fit between the wetting fluid container and the inlet of the wetting receptacle.

According to a third aspect of the invention there is provided a fluid container for use with a receptacle having an inlet and a fluid receiving area in fluid communication with the inlet, the fluid container comprising a forward portion which is adapted to be positioned in the inlet of the receptacle and comprises a discharge outlet movable on application of a predetermined condition thereto from a closed position in which the fluid is retained in the fluid container to an open position in which the fluid is dischargeable forwardly from the forward portion of the fluid container, the predetermined condition able to be applied to the discharge outlet when the forward portion of the fluid container is positioned in the inlet to enable the fluid contained in the fluid container to be discharged into the fluid receiving area of the receptacle. The fluid container therefore alleviates the problem of spillage on discharge of the contents into the fluid receiving area.

In an embodiment of the invention according to its third aspect hereinafter to be described the fluid container is for use with a receptacle whose fluid receiving area is adapted in use to receive a hydrophilic urinary catheter and the fluid container contains a fluid which on discharge into the fluid receiving area wets the hydrophilic coating of the catheter.

In an embodiment of the invention hereinafter to be described the fluid container comprises predetermined condition applying means for applying the predetermined condition to the discharge outlet to bring the discharge outlet to the open position.

In an embodiment of the invention hereinafter to be described the forward portion of the fluid container is positioned in the inlet of the receptacle when the fluid container is in the operational position, the fluid container comprises a rearward portion which in the operational position of the fluid container projects from the inlet of the receptacle and the rearward portion comprises at least a part of the predetermined condition applying means.

In an embodiment of the invention hereinafter to be described the discharge outlet comprises an area of weakness in the material of the forward portion of the fluid container which on application of a predetermined force thereto is brought to the open position.

In an embodiment of the invention hereinafter to be described the at least a part of the predetermined condition applying means comprised of the rearward portion of the fluid container is a tab which on application of a predetermined pulling force thereto causes the predetermined force to be applied to the area of weakness in the material of the forward portion of the fluid container.

In an embodiment of the invention hereinafter to be described the area of weakness in the material of the forward portion of the fluid container is a tear line which is torn on application of the predetermined pulling force to the tab. The predetermined condition applying means further comprises holding means for holding the fluid container in the operational position against the action of the predetermined pulling force applied to the tab.

In an embodiment of the invention hereinafter to be described the receptacle is of a flexible material and the holding means is provided on the forward portion to be gripped by a user through the material of the receptacle when the fluid container is in the operational position.

In an embodiment of the invention hereinafter to be described the forward portion of the fluid container presents a forward edge, the tear line extends rearwardly from the forward edge, the tab is a first tab which extends rearwardly from the forward edge of the forward portion on a first side of the tear line and is of such dimensions that when the fluid container is in the operational position the first tab projects from the inlet of the receptacle, the holding means for holding the fluid container in the operational position against the action of the pulling force applied to the first tab is a second tab which extends forwardly from the forward edge on a second opposite side of the tear line and application of a predetermined rearward pulling force on the first tab relative to the second tab causes the tear line to tear and the fluid to be dischargeable from the fluid container into the fluid receiving area of the receptacle.

In embodiments of the invention hereinafter to be described the fluid container takes the form of a sachet.

In an embodiment of the invention according to its third aspect hereinafter to be described the fluid container is adapted to be integrated with the receptacle by friction fit in the inlet of the receptacle to maintain the fluid container in the operational position. An integrated unit is thus obtained having the benefits of the apparatus according to the first and second aspects of the invention.

In an embodiment of the invention according to its third aspect the fluid container contains water or saline and is made of aluminium foil, poly(vinylidene chloride) or a metallised film such as metallised poly(ethylene terepthalate).

The present invention has the advantage of providing a safe, compact, sterile and disposable wetting apparatus for a hydrophilic urinary catheter which is easy to handle. This is due to the provision of a wetting fluid container component part which is adapted to cooperate with a wetting receptacle component part of the apparatus so as to be able to release its contents into the wetting receptacle to wet a hydrophilic urinary catheter placed therein under clean conditions, that is to say, without the need for touching of the catheter, fluid or inner surface of the wetting receptacle thereby avoiding or alleviating the risk of introducing contaminants.

BRIEF DESCRIPTION OF THE DRAWINGS

By way of example embodiments of the invention will now be described with reference to the accompanying drawings in which:

FIG. 2 shows a wetting apparatus according to a second embodiment of the invention comprising a urine collection bag and an unopened wetting fluid sachet in accordance with the invention integrated therewith in an operational position in the inlet of the urine collection bag;

FIG. 3 is an exploded view of the unopened sachet of the wetting apparatus shown in FIG. 2 in the operational position in the inlet of the urine collection bag;

FIG. 7 corresponds to FIG. 2 but with the wetting fluid sachet having been opened; and FIG. 8 corresponds to FIG. 3 but with the wetting fluid sachet having been opened.

DETAILED DESCRIPTION

Figure 1:
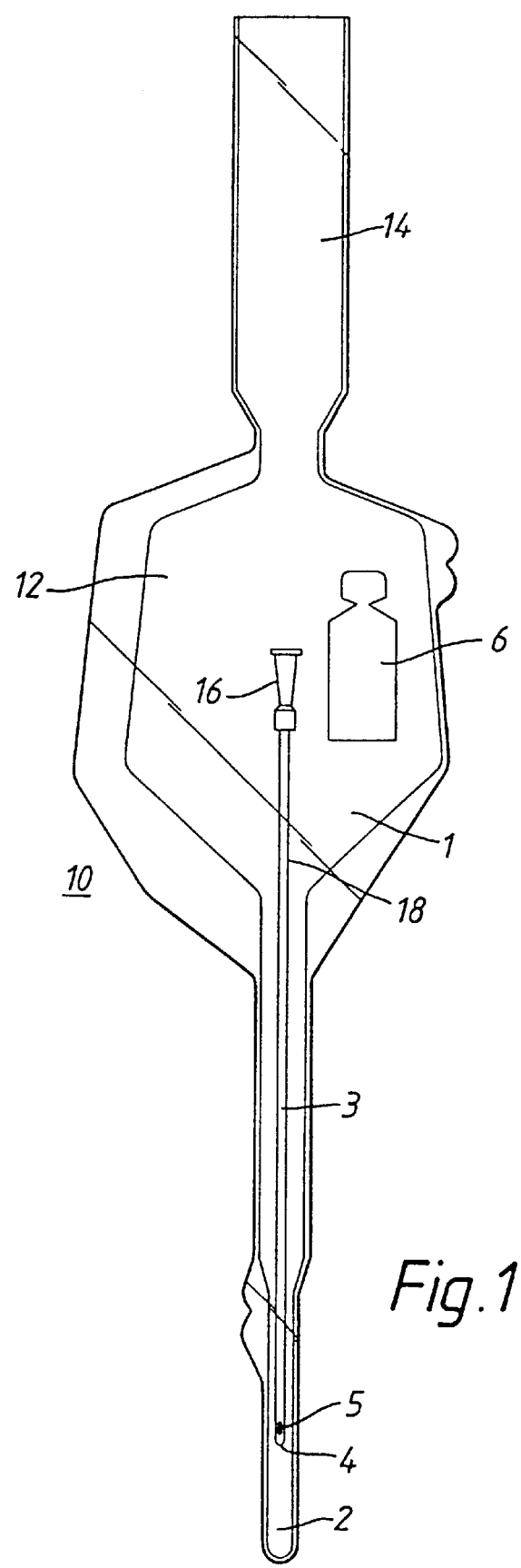
FIG. 1 shows a wetting apparatus according to a first embodiment of the invention comprising a urine collection bag and a wetting fluid container integrated therewith.

Referring first to FIG. 1, there is shown a wetting apparatus 10 according to the invention comprising a urine collection bag 1 of a transparent flexible plastics material. The bag 1 presents at the forward end thereof an elongate pocket 2 of depth sufficient to receive at least the insertable length of a hydrophilic urinary catheter 3. The urine collection bag 1 further defines to the rear of the pocket 2 a urine collection chamber 12 which is in fluid communication with the pocket 2. Further rearwardly is an inlet 14 to the urine collection bag 1 through which the hydrophilic urinary catheter 3 is able to be introduced into the bag 1.

As can be seen, the catheter 3 comprises a flared rearward portion 16 and an elongate shaft 18 which extends forwardly from the rearward portion 16 and terminates in a rounded tip 4 at the forward end thereof The catheter 3 is provided with a lumen (not shown) which extends from an open end in the rearward portion 16 to a drainage aperture 5 in the tip 4.

A container in the form of a sachet 6 is secured to the inner surface of the urine bag 1. The sachet 6 contains sterile water or saline or other fluid suitable for wetting the hydrophilic urinary catheter 3 and is pierceable or otherwise openable, for example by applying a hand pressure, so as to release substantially all of the water or saline contained therein into the pocket 2 immediately prior to use of the catheter 3.

Typically, the urine collection bag 1 with integrated sachet 6 and, where pre-packaged therewith, the catheter 3 will be sterilised using ethylene oxide. Since the sachet 6 contains sterile water or saline there is no need for sterilising the contents of the sachet 6. Accordingly, the material of the sachet 6 is preferably impermeable to ethylene oxide and water. Non-limiting examples of materials meeting these requirements are poly(vinylidene chloride) (PVDC), aluminium foil laminates and metallised films, for example metallised poly(ethylene terepthalate). Other sterilisation processes could of course be used instead, for example by irradiation in which case the fluid in the sachet 6 could be sterilised in situ at the same time as the rest of the components of the apparatus 10.

The volume of the sachet 6 is sufficient to release such an amount of water or saline into the pocket 2 to enable wetting of the insertable length of the catheter 3 immediately prior to use. By "insertable length" is meant at least that length of the elongate shaft 18 which is coated with a hydrophilic material, for example PVP, and inserted into the urethra of the patient. Typically, this will be 80–140 mm for a female patient and 200–350 mm for a male patient.

The holding time of the catheter 3 in the pocket 2 may vary within a broad range but will typically amount to at least 30 seconds.

The location of the sachet 6 inside the bag 1 is not critical as long as the sachet 6 releases its contents into the pocket 2. It is preferred, though, that the sachet 6 be disposed as close to the open end of the pocket 2 as possible. In this embodiment the sachet 6 is permanently fixed in position in the urine collection bag 1, for example by adhesion to the bag 1. It will be appreciated, however, that the sachet 6 could in fact be freely movable in the bag 1. The fundamental point is that the sachet 6 is within the bounds of the bag 1 so that the two components form an integrated unit.

In use, the catheter 3 is introduced into the bag 1 through the inlet 14 and the elongate shaft 18 manoeuvred into the pocket 2 as shown. The inlet 14 is then sealed, for example by tying a knot in the material defining the inlet 14 or by clamping the inlet 14 with a clamp. The sachet 6 is then opened, for example by applying a pressure thereto through the material of the bag 1, to release the wetting fluid into the pocket 2 and the catheter 3 left to soak for a predetermined duration in the wetting fluid to wet the hydrophilic outer surface thereof Alternately, the bag 1 may be provided with a closed end in place of the inlet with the catheter 3 pre-packaged inside the bag 1. An inlet 14 is preferred, though, where ethylene oxide is the sterilising agent as this provides a pathway for the ethylene oxide to enter and exit the inside of the bag 1.

After wetting of the catheter 3 for the predetermined duration, the bag 1 is turned upside down and the forwardmost portion of the pocket 2 torn off. The elongate shaft 18 of the catheter 3 is then manoeuvred through the opening in the forward end of the pocket 2 and into the urethra of the patient until the flared rearward portion 16 forms a mechanical seal connection with the opening. There is therefore no need to directly handle the catheter 3 for insertion thereof into the urethra which is to advantage as the outer surface of the catheter 3 will be slippery due to the wetting procedure and therefore difficult to grip and furthermore because the possibility of contamination of the catheter 3 at this stage is avoided.

Urine in the bladder of the patient is transported rearwardly through the lumen of the catheter 3 into the urine collection chamber 12. The catheter 3 is manoeuvred back inside the bounds of the bag 1 and the open end of the pocket 2 closed off for example by tying a knot with the material defining the pocket 2 or clamping the pocket 2 with a clamp. An opening can then be made in the urine collection chamber 12 for the collected urine to be poured away after which the bag 1 can be disposed of.

Turning now to FIGS. 2 and 3 of the drawings, there is shown an alternative wetting apparatus 110 according to the present invention. The wetting apparatus 110 comprises a urine collection bag 101 of a flexible transparent plastics material which corresponds to the urine collection bag 1 of the wetting apparatus 10 hereinbefore described with reference to FIG. 1 of the drawings. That is to say, the urine collection bag 101 has a downwardly extending elongate pocket 102 at the forward end, a urine collection chamber 112 rearwardly of and in fluid communication with the elongate pocket 102 and an inlet 114 to the bag 101 spaced further rearwardly.

Again as in the wetting apparatus 10 hereinbefore described with reference to FIG. 1, a hydrophilic urinary catheter 103 having a flared rearward portion 116, an elongate shaft 118 projecting forwardly from the rearward portion 116 and an open-ended lumen (not shown) which extends from the rear end of the rearward portion 116 to a drainage aperture 105 in the rounded tip 104 at the forward end of the catheter 103 is able to be inserted into the urine collection bag 101 through the inlet 114 such that preferably at least the insertable length of the catheter 103 is received in the pocket 102.

As can be seen more particularly by reference to FIG. 3, a wetting fluid containing sachet 106 is inserted into the inlet 114 to an operational position in which it is held in place by a friction fit. The sachet 106 has a forward portion 120 which in the operational position of the sachet 106 projects forwardly into the inlet 114 and a rearward portion 122 which in the operational position projects rearwardly out of the inlet 114.

The sachet 106 is preferably made of aluminium foil, particularly when ethylene oxide is the sterilising agent for the apparatus 110 and the sachet contains sterile water or saline solution. Where ethylene oxide is the sterilising agent for the apparatus 110 the fit of the sachet 106 in the inlet 114 is not so tight as to prevent ethylene oxide from entering and exiting the inside of the bag 101 and sterilising the inner surface of the bag 101 and outer surfaces of the sachet 106 and catheter 103. The wetting fluid is retained in the sachet 106 by peripheral sealing of the sachet 106 as shown.

Figure 4:
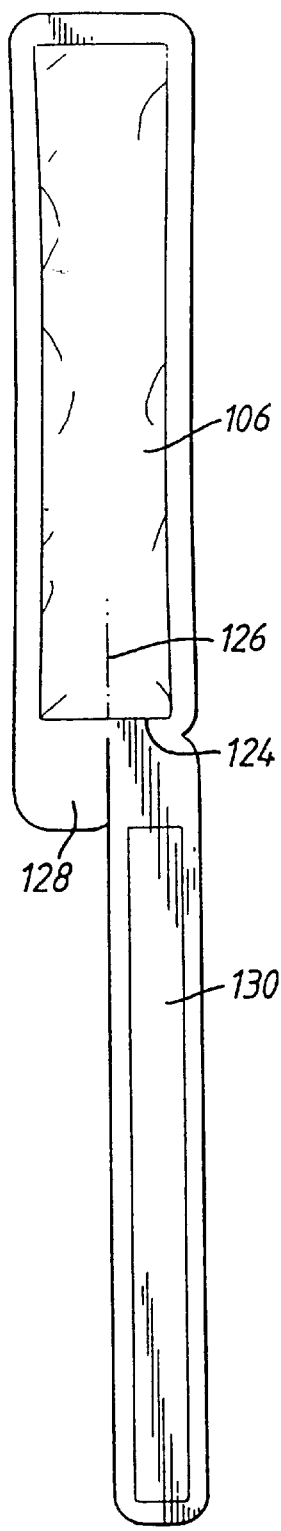
FIG. 4 is a front view of the unopened sachet of the wetting apparatus shown in FIG. 2 in an extended configuration prior to insertion thereof into the inlet of the urine collection bag to the operational position.
Figure 5:
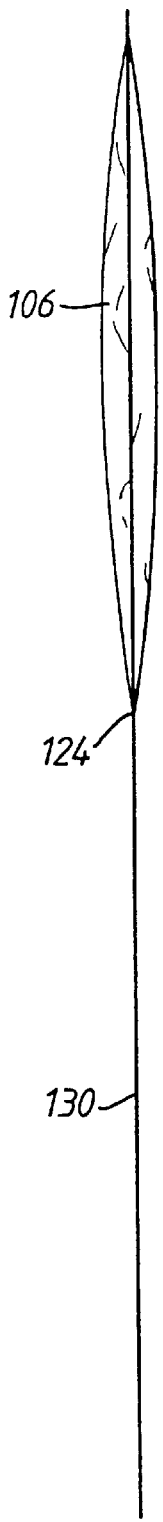
FIG. 5 is a side view of the unopened sachet shown in FIG. 4.

Referring now to FIGS. 4 and 5, the forward portion 120 of the sachet 106 presents a forward edge 124. Extending rearwardly from the forward edge 124 is a tear line 126. Projecting forwardly from the forward edge 124 of the sachet 106 to one side of the tear line 126 is a first tab 128. On the other side of the tear line 126 there is provided an elongate second tab 130 shown here in an extended position in which the second tab 130 projects forwardly from the forward edge 124.

Figure 6:
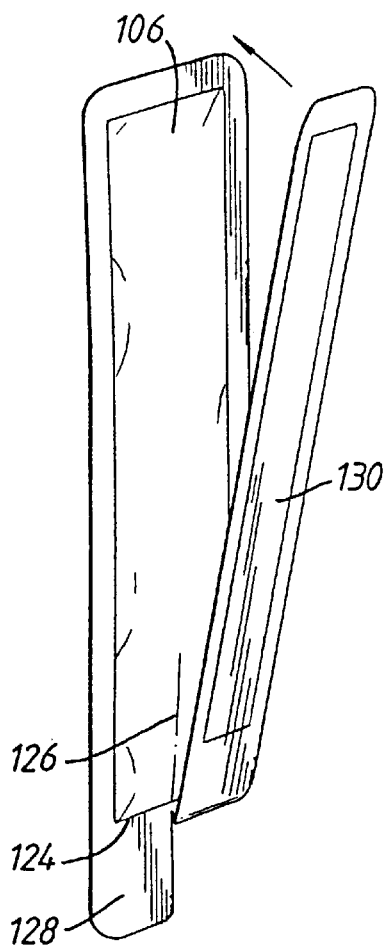
FIG. 6 is a perspective view of the unopened sachet of the wetting apparatus shown in FIG. 2 in a retracted configuration ready for insertion into the inlet of the urine collection bag to the operational position.

As shown in FIG. 6, the elongate second tab 130 is movable about the forward edge 124 back on its self from the extended position shown in FIGS. 4 and 5 to a retracted position in which the second tab 130 extends rearwardly from the forward edge 124. When the second tab 130 is in the retracted position the sachet 106 is inserted into the inlet 114 to the operational position shown in FIGS. 2 and 3.

Returning now to FIGS. 2 and 3, it can be seen that the dimensions of the second tab 130 are such that when the sachet 106 is in the operational position a pulling portion 132 of the second tab 130 projects rearwardly from the inlet 114 of the urine collection bag 101 and forms a part of the rearward portion 122 of the sachet 106.

In FIGS. 7 and 8 there is shown the operation of the sachet 106 to release the contents of the sachet 106 into the pocket 102 to wet the hydrophilic outer coating of the catheter 103. The user grips the first tab 128 through the flexible transparent plastics material of the bag 101 and then pulls rearwardly on the pulling portion 132 of the second tab 130 which projects from the inlet 114 to cause the tear line 126 to be torn and the wetting fluid to be released into the pocket 102 to wet the catheter 103. Preferably, the sachet 106 contains sufficient wetting fluid for the pocket 102 to be filled to a level which results in the insertable length of the catheter 103 being wetted .

After release of the wetting fluid into the pocket 102 the sachet 106 is removed from the bag 101 and disposed of. The bag 101 and catheter 103 are then utilised in the manner hereinabove described for the wetting apparatus 10 shown in FIG. 1.

If need be, the bag 101 can be a closed bag with the sachet 106 and catheter 103 pre-packaged within the bag 101. In this instance, the construction of the bag 101 is such that the sachet 106 can be opened in the aforementioned manner through the material of the bag 101.

The wetting apparatus 110 described hereinabove with reference to FIGS. 2 to 8 has the advantage of inter alia (i) being environmentally friendly in the sense that where the sachet 106 is made of Al foil the sachet is able to be disposed of separately from the bag 101 thus facilitating recycling of the Al foil; and (ii) having a sachet 106 which can better withstand the cyclical pressures which are typically exerted on wetting apparatus when packaged and subjected to a sterilising process as a consequence of the sachet 106 not having to be opened through application of a direct pressure thereto through the material of the bag 101 in which case a significantly weakened sachet edge would be required as a high pressure could not be applied through the bag 101 without damaging the bag 101.

In the exemplary embodiments hereinabove described with reference to the Figures of drawings the supply of wetting fluid for wetting of the hydrophilic urinary catheter takes the form of a separate sachet integrated into the wetting receptacle. It will be appreciated by those versed in the art that the supply could also take the form of an integrally formed chamber in the material of the wetting receptacle without departing from the spirit of the invention.

What is claimed is:

1. A wetting apparatus for wetting a hydrophilic urinary catheter prior to use comprising:
    a wetting receptacle which defines a wetting fluid receiving area, wherein the wetting fluid receiving area forms an elongate pocket having a volume therein,
    a urinary catheter arranged in said wetting receptacle, wherein the urinary catheter has a proximal and distal end and a hydrophilic outer surface on at least an insertable length of the catheter, and wherein the elongate pocket accommodates the insertable length of the catheter, and
    a wetting fluid container containing a wetting fluid and having a discharge outlet movable from a closed position to an open position on application of a predetermined condition thereto to enable the wetting fluid to be discharged from the wetting fluid container, wherein:
    the wetting fluid container is integrated with the wetting receptacle;
    at least the discharge outlet of the wetting fluid container is disposed within the wetting receptacle;
    the discharge outlet of the wetting fluid container is in fluid communication with the wetting fluid receiving area; and
    an application of the predetermined condition to the discharge outlet of the wetting fluid container enables the wetting fluid to be discharged into the wetting fluid receiving area and, thereby, to wet at least the insertable length of the hydrophilic urinary catheter.

2. The wetting apparatus according to claim 1, wherein the wetting fluid container contains sufficient wetting fluid to fill the elongate pocket to a level for wetting at least the insertable length of the hydrophilic urinary catheter.

3. The wetting apparatus according to claim 2, wherein the wetting receptacle is a urine collection bag, and the elongate pocket forms a forward portion thereof.

4. The wetting apparatus according to claim 3, wherein the urine collection bag further comprises a urine collection chamber located at a rear portion of the elongate pocket, said urine collection chamber having a volume greater than the volume of the elongate pocket.

5. A The wetting apparatus according to claim 4, wherein the elongate pocket of the urine collection bag presents an open rear end and a weakened closed forward end which is removable upon application of a predetermined pressure thereto thereby to enable a portion of the hydrophilic urinary catheter comprising at least the insertable length thereof to be projected through a forward end of the elongate pocket after wetting thereof for insertion into the urethra of a patient, and that the urine collection chamber having a forward end which is in fluid communication with the open rear end of the elongate pocket and being adapted in use to collect urine transported rearwardly through the hydrophilic urinary catheter after insertion thereof into the urethra of the patient.

6. The wetting apparatus according to claim 1, wherein the wetting fluid container is made of aluminum foil, poly (vinylidene chloride) or a metallicized film.

7. The wetting apparatus according to claim 6, wherein the metallized film comprises metallized poly(ethylene terephthalate).

8. The wetting apparatus according to any one of the preceding claims, wherein the wetting fluid container is fully contained within the wetting receptacle.

9. The wetting apparatus according to claim 8, wherein the wetting fluid container is permanently fixed to an inner surface of the wetting receptacle.

10. The wetting apparatus according to claim 8, wherein the wetting fluid container is an integrally formed compartment of the wetting receptacle.

11. The wetting apparatus according to claim 1, wherein the wetting receptacle is formed of a flexible material and that the discharge outlet of the wetting fluid container is able to be brought to the open position through application of a predetermined force to the wetting fluid container through the flexible material of the wetting receptacle.

12. The wetting apparatus according to claim 1, wherein the wetting fluid container is integrated with the wetting receptacle in a releasably secured manner.

13. The wetting apparatus according to claim 12, wherein the wetting receptacle is provided with an inlet which is in fluid communication with the wetting fluid receiving area and that the wetting fluid container is releasably secured in the inlet of the wetting receptacle by insertion of at least a forward portion thereof in the inlet, the forward portion of the wetting fluid container presenting the discharge outlet.

14. The wetting apparatus according to claim 13, wherein the wetting fluid container is releasably secured in the inlet of the wetting receptacle through a friction fit between the wetting fluid container and the inlet of the wetting receptacle.

15. The wetting apparatus according to claim 14, wherein the wetting fluid container comprises means for applying the predetermined condition to the discharge outlet to bring the discharge outlet of the wetting fluid container to its open position.

16. The wetting apparatus according to claim 15, wherein the forward portion of the wetting fluid container is positioned in the inlet of the wetting receptacle, and that the wetting fluid container comprises a rearward portion which projects from the inlet of the wetting receptacle.

17. The wetting apparatus according to claim 16, wherein the rearward portion comprises at least a part of the means for applying the predetermined condition.

18. The wetting apparatus according to claim 17, wherein the discharge outlet comprises an area of weakness in the material of the forward portion of the wetting fluid container which on application of a predetermined force thereto is able to be brought to the open position.

19. The wetting apparatus according to claim 18, wherein at least a part of the means for applying the predetermined condition comprised of the rearward portion of the wetting fluid container is a tab which on application of a predetermined pulling force thereto causes the predetermined force to be applied to an area of weakness in the material of the forward portion of the wetting fluid container.

20. The wetting apparatus according to claim 19, wherein the area of weakness in the material of the forward portion of the wetting fluid container is a tear line which is adapted to be torn on application of the predetermined pulling force to the tab.

21. The wetting apparatus according to claim 20, wherein the means for applying the predetermined condition further comprises holding means for holding the wetting fluid container against the action of the predetermined pulling force applied to the tab.

22. The wetting apparatus according to claim 21, wherein the wetting receptacle is of a flexible material and that the holding means is provided on the forward portion to be gripped by a user through the flexible material of the wetting receptacle.

23. The wetting apparatus according to claim 22, wherein the forward portion of the wetting fluid container presents a forward edge, that the tear line extends rearwardly from the forward edge, that the tab is a first tab which extends rearwardly from the forward edge of the forward portion on a first side of the tear line and being of such dimensions as to project from the inlet of the wetting receptacle, that the holding means for holding the wetting fluid container against the action of the pulling force applied to the first tab is a second tab which extends forwardly from the forward edge on a second opposite side of the tear line and that application of a predetermined rearward pulling force on the first tab relative to the second tab causes the tear line to tear and the wetting fluid to discharge from the wetting fluid container into the wetting fluid receiving area of the wetting receptacle.

24. The wetting apparatus according to claim 1, wherein the wetting fluid container takes the form of a sachet.

25. The wetting apparatus according to claim 1, wherein the wetting fluid is water or a saline solution.

26. The wetting apparatus according to claim 25, wherein the wetting fluid container is made of a material which is impermeable to ethylene oxide and water or saline solution.

* * * * *

UNITED STATES PATENT AND TRADEMARK OFFICE
CERTIFICATE OF CORRECTION

PATENT NO. : 6,736,805 B2  
DATED : May 18, 2004  
INVENTOR(S) : Anette Israelsson et al.

It is certified that error appears in the above-identified patent and that said Letters Patent is hereby corrected as shown below:

Title page,  
Item [56], References Cited, U.S. PATENT DOCUMENTS, "2,872,433" reference, "4/1959" should be -- 2/1959 --; and "5,147,341" reference, "9/1992" should be -- 8/1992 --.  
FOREIGN PATENT DOCUMENTS, after the four listed documents insert the following:

-- 
| | | |
|---|---|---|
| AU | 0 710 581 | 4/1998 |
| AU | 0 710 966 | 5/1998 |
| CN | 1 106 744 | 8/1995 |
| DK | 0 122 4496 | 3/1998 |
| EP | 0 064 747 | 11/1982 |
| EP | 0 093 093 | 11/1983 |
| EP | 0 159 034 | 10/1985 |
| EP | 0 168 917 | 1/1986 |
| EP | 0 217 771 | 4/1987 |
| EP | 0 282 273 | 9/1988 |
| EP | 0 289 996 | 11/1988 |
| EP | 0 336 984 | 10/1989 |
| EP | 0 423 855 | 4/1991 |
| EP | 0 440 427 | 8/1991 |
| EP | 0 483 941 | 5/1992 |
| EP | 0 566 755 | 10/1993 |
| EP | 0 591 091 | 4/1994 |
| EP | 0 592 870 | 4/1994 |
| EP | 0 629 415 | 12/1994 |
| EP | 0 677 299 | 10/1995 |
| EP | 0 680 895 | 11/1995 |
| EP | 0 685 179 | 12/1995 |
| EP | 0 923 478 | 6/1999 |
| FR | 2 447 328 | 8/1980 |
| DE | 23 17 839 | 10/1974 |
| DE | 94 13 716.1 | 12/1994 |
| GB | 1 436 679 | 5/1976 |
| GB | 1 465 544 | 2/1977 |
| GB | 1 498 356 | 1/1978 |
| GB | 1 561 569 | 2/1980 |
| GB | 1 600 963 | 10/1981 |
| GB | 1 601 691 | 11/1981 |
| GB | 2 033 231 | 5/1980 |
| GB | 2 075 347 | 11/1981 |
| GB | 2 156 680 | 10/1985 |

UNITED STATES PATENT AND TRADEMARK OFFICE
CERTIFICATE OF CORRECTION

PATENT NO.    : 6,736,805 B2
DATED         : May 18, 2004
INVENTOR(S)   : Anette Israelsson et al.

It is certified that error appears in the above-identified patent and that said Letters Patent is hereby corrected as shown below:

FOREIGN PATENT DOCUMENTS, cont'd.,

| | | |
|---|---|---|
| JP | 55-12265 | 3/1980 |
| WO | 89/02763 | 4/1989 |
| WO | 89/09246 | 10/1989 |
| WO | 90/01345 | 2/1990 |
| WO | 92/07607 | 5/1992 |
| WO | 94/06377 | 3/1994 |
| WO | 94/16747 | 8/1994 |
| WO | 94/26336 | 11/1994 |
| WO | 95/02374 | 1/1995 |
| WO | 95/23619 | 9/1995 |
| WO | 96/23600 | 8/1996 |
| WO | 96/30277 | 10/1996 |
| WO | 97/26937 | 7/1997 |
| WO | 97/47349 | 12/1997 |
| WO | 98/06642 | 2/1998 |
| WO | 98/11932 | 3/1998 |
| WO | 98/19729 | 5/1998 |
| RU | 2 012 370 | 5/1994 |
| SE | 0 398 048 | 12/1977 |
| SE | 0 439 110 | 6/1985 |
| SE | 7 403 861-3 | 12/1977 |

OTHER PUBLICATIONS, insert the following:

-- "Promoting incontinence: the role of the nurse, part 2," Nursing Times, Vol. 90, No. 45, 5-8, Nov. 1994.

Asayama, K. et al., "The functional limitations of tetraplegic hands for intermittent clean self-catherisation," Paraplegie, No. 33, 30-33, Jan. 1995.

Astra Tech Inc., "LoFric: The low friction intermittent catheterization" brochure, 1992.

Blitz, B., "A simple method using hydrophilic guide wires for the difficult urethral catheterization," J Urol, Vol. 46, No. 1, 99-100, 1995.

Charbonneau-Smith, R., "No touch catheterization and infection rates in a select spinal cord injured population," Rehabilitating Nursing, Vol. 18, No. 5, 296-9, 305, 355-6, Sep-Oct. 1999.

UNITED STATES PATENT AND TRADEMARK OFFICE
CERTIFICATE OF CORRECTION

PATENT NO. : 6,736,805 B2
DATED : May 18, 2004
INVENTOR(S) : Anette Israelsson et al.

It is certified that error appears in the above-identified patent and that said Letters Patent is hereby corrected as shown below:

OTHER PUBLICATIONS, cont'd.,

Deegan, S., "Close to normality ... intermittent catheterisation," Nursing Times, Vol. 87, No. 44, 65-67, Oct. 1991.

Deegan, S., "Intermittent catheterisation for children," Nursing Times, Vol. 82, No. 14, 72-74, Apr. 1985.

Diokno, A. et al., "Patient satisfaction and the Iofric catheter for clean intermittent catheterization" J. Urol, Vol. 153, No. 2, 349-351, Feb. 1995.

Getliffe, K., "Long term catheter use in the community," Nursing Standard, Vol. 9, No. 31, 25-27, April 1995.

Grose, K., "Urological community nursing: a new concept in the delivery of urological care," Br J Urol, No. 76, 440-442, 1995.

Haynes, S., "Intermittent self-catheterisation - the key facts," Professional Nurse, Vol. 10, No. 2, 100-104, Nov. 1994.

Hellstrom, P. et al., "Efficacy and safety of cleaning intermittent catheterisation in adults," Eur Urol, No. 20, 117-121, 1991.

Kennedy, A., "Incontinence advice: long term catheterisation part 1," Nursing Times, Vol. 79, No. 17, 41-45, Apr. 1983.

Mattelaer, J., "Catheter and sounds: the history of bladder catheterisation," Paraplegia, No. 33, 429-433, Aug. 1995.

McSweeney, P., "Self-catheterisation - a solution for some incontinent people," Professional Nurse, No. 8, 399-401, May 1989.

Moore, K., "Intermittent self-catheterisation research-based practice," British Journal of Nursing, Vol. 4, No. 18, 1057-8, 1060, 1062-3, 1995.

Oldbury, M., "Hard won comfort... self-catheterisation," Nursing Times, Vol. 88, No. 13, 86, March 1992.

Oliver, H., "The treatment of choice... intermittent self-catheterisation," Nursing Times, Vol. 84, No. 31, 70, Aug. 1988.

UNITED STATES PATENT AND TRADEMARK OFFICE
CERTIFICATE OF CORRECTION

PATENT NO. : 6,736,805 B2
DATED : May 18, 2004
INVENTOR(S) : Anette Israelsson et al.

It is certified that error appears in the above-identified patent and that said Letters Patent is hereby corrected as shown below:

OTHER PUBLICATIONS, cont'd.,

Perkash, I. et al., "Clean intermittent catheterisation in spinal cord injured patients: a follow up study," J. Urol, Vol. 149, 1068-1071, 1993.

Perrouin-Verbe, B. et al., "Clean intermittent catheterisation from the acute period in spinal cord injury patients. Long term evaluation of urethral and genital tolerance," Paraplegia, No. 33, 619-624, 1995.

Rainville, N., "The current nursing procedure for intermittent urinary catheterization n in rehbilitation facilities," Rehabilitation Nursing, Vol. 19, No. 6, 330-3, 382, Nov.-Dec. 1994.

Sibley, L., "Confidence with incontinence," Nursing Times, Vol. 84, No. 46, 42-43, Nov. 1988.

Vaidyanathian, S. et al., "Urethral cytology in spinal cord injury patients performing intermittent catheterisation," Paraplegia, No. 32, 493-500, 1994.

Waller, L. et al., "Clean intermittent catheterisation in spinal cord injury patients: long term followup of a hydrophilic low friction technique," J.Urol, Vol. 153, No. 2, 345-348, February 1995.

Webb, R. et al., "Clean intermittent self-catheterisation in 172 adults," Br. J Urol, Vol. 65, 20-23, 1990.

Willis, J., "Intermittent catheters," Professional Nurse, Vol. 10, No. 8, 523-524, May 1995.

Winder, A., "Intermittent self-catheterisation," Nursing Times, Vol. 86, No. 43, 63-4, Oct. 1990.

Winder, A., "Achieving independence... self-catheterisation," Nursing Times, Vol. 90, No. 22, 50-51, June 1994.

UNITED STATES PATENT AND TRADEMARK OFFICE
CERTIFICATE OF CORRECTION

PATENT NO. : 6,736,805 B2
DATED : May 18, 2004
INVENTOR(S) : Anette Israelsson et al.

It is certified that error appears in the above-identified patent and that said Letters Patent is OTHER PUBLICATIONS, cont'd.,

```
    Wyndaele, J. et al., "Clean Intermittent self-
catheterisation: a 12 year follow up," J.Urol, Vol. 143,
906-908, Nov. 1989.
```

Column 2,
Line 4, after "OF" should be inserted -- THE --.

Column 6,
Line 49, "thereof" should be -- thereof. --.

Column 7,
Line 36, "thereof" should be -- thereof. --.

Signed and Sealed this

Thirtieth Day of November, 2004

JON W. DUDAS
*Director of the United States Patent and Trademark Office*

UNITED STATES PATENT AND TRADEMARK OFFICE
CERTIFICATE OF CORRECTION

PATENT NO. : 6,736,805 B2
DATED : May 18, 2004
INVENTOR(S) : Anette Israelsson et al.

It is certified that error appears in the above-identified patent and that said Letters Patent is hereby corrected as shown below:

Title page,
Item [56], References Cited, U.S. PATENT DOCUMENTS, "2,872,433" reference, "4/1959" should be -- 2/1959 --; and "5,147,341" reference, "9/1992" should be -- 8/1992 --.
FOREIGN PATENT DOCUMENTS, after the four listed documents insert the following:

```
-- AU      0 710 581       4/1998
   AU      0 710 966       5/1998
   CN      1 106 744       8/1995

DK      0 102 396       8/1965
   DK      0 122 496       3/1998
   EP      0 064 747      11/1982
   EP      0 093 093      11/1983
   EP      0 159 034      10/1985
   EP      0 168 917       1/1986
   EP      0 217 771       4/1987
   EP      0 282 273       9/1988
   EP      0 289 996      11/1988
   EP      0 336 984      10/1989
   EP      0 423 855       4/1991
   EP      0 440 427       8/1991
   EP      0 483 941       5/1992
   EP      0 566 755      10/1993
   EP      0 591 091       4/1994
   EP      0 592 870       4/1994
   EP      0 629 415      12/1994
   EP      0 677 299      10/1995
   EP      0 680 895      11/1995
   EP      0 685 179      12/1995
   EP      0 923 478       6/1999

FR      2 447 328       8/1980
   DE     23 17 839       10/1974
   DE     94 13 716.1     12/1994
   GB      1 436 679       5/1976
   GB      1 465 544       2/1977
   GB      1 498 356       1/1978
   GB      1 561 569       2/1980
   GB      1 600 963      10/1981
   GB      1 601 691      11/1981
   GB      2 033 231       5/1980
   GB      2 075 347      11/1981
   GB      2 156 680      10/1985
   JP        47-19193      2/1972
```

UNITED STATES PATENT AND TRADEMARK OFFICE
CERTIFICATE OF CORRECTION

PATENT NO. : 6,736,805 B2
DATED : May 18, 2004
INVENTOR(S) : Anette Israelsson et al.

It is certified that error appears in the above-identified patent and that said Letters Patent is hereby corrected as shown below:

FOREIGN PATENT DOCUMENTS, cont'd.,

| | | |
|---|---|---|
| JP | 55-12265 | 3/1980 |
| WO | 89/02763 | 4/1989 |
| WO | 89/09246 | 10/1989 |
| WO | 90/01345 | 2/1990 |
| WO | 92/07607 | 5/1992 |
| WO | 94/06377 | 3/1994 |
| WO | 94/16747 | 8/1994 |
| WO | 94/26336 | 11/1994 |
| WO | 95/02374 | 1/1995 |
| WO | 95/23619 | 9/1995 |
| WO | 96/23600 | 8/1996 |
| WO | 96/30277 | 10/1996 |
| WO | 97/26937 | 7/1997 |
| WO | 97/47349 | 12/1997 |
| WO | 98/06642 | 2/1998 |
| WO | 98/11932 | 3/1998 |
| WO | 98/19729 | 5/1998 |
| RU | 2 012 370 | 5/1994 |
| SE | 0 398 048 | 12/1977 |
| SE | 0 439 110 | 6/1985 -- |

OTHER PUBLICATIONS, insert the following:

-- "Promoting incontinence: the role of the nurse, part 2," Nursing Times, Vol. 90, No. 45, 5-8, Nov. 1994.

Asayama, K. et al., "The functional limitations of tetraplegic hands for intermittent clean self-catherisation," Paraplegie, No. 33, 30-33, Jan. 1995.

Astra Tech Inc., "LoFric: The low friction intermittent catheterization" brochure, 1992.

Blitz, B., "A simple method using hydrophilic guide wires for the difficult urethral catheterization," J Urol, Vol. 46, No. 1, 99-100, 1995.

Charbonneau-Smith, R., "No touch catheterization and infection rates in a select spinal cord injured population," Rehabilitating Nursing, Vol. 18, No. 5, 296-9, 305, 355-6, Sep-Oct. 1999.

UNITED STATES PATENT AND TRADEMARK OFFICE
CERTIFICATE OF CORRECTION

PATENT NO. : 6,736,805 B2
DATED : May 18, 2004
INVENTOR(S) : Anette Israelsson et al.

It is certified that error appears in the above-identified patent and that said Letters Patent is hereby corrected as shown below:

OTHER PUBLICATIONS, cont'd.,

Deegan, S., "Close to normality ... intermittent catheterisation," Nursing Times, Vol. 87, No. 44, 65-67, Oct. 1991.

Deegan, S., "Intermittent catheterisation for children," Nursing Times, Vol. 82, No. 14, 72-74, Apr. 1985.

Diokno, A. et al., "Patient satisfaction and the Iofric catheter for clean intermittent catheterization" J. Urol, Vol. 153, No. 2, 349-351, Feb. 1995.

Getliffe, K., "Long term catheter use in the community," Nursing Standard, Vol. 9, No. 31, 25-27, April 1995.

Grose, K., "Urological community nursing: a new concept in the delivery of urological care," Br J Urol, No. 76, 440-442, 1995.

Haynes, S., "Intermittent self-catheterisation - the key facts," Professional Nurse, Vol. 10, No. 2, 100-104, Nov. 1994.

Hellstrom, P. et al., "Efficacy and safety of cleaning intermittent catheterisation in adults," Eur Urol, No. 20, 117-121, 1991.

Kennedy, A., "Incontinence advice: long term catheterisation part 1," Nursing Times, Vol. 79, No. 17, 41-45, Apr. 1983.

Mattelaer, J., "Catheter and sounds: the history of bladder catheterisation," Paraplegia, No. 33, 429-433, Aug. 1995.

McSweeney, P., "Self-catheterisation - a solution for some incontinent people," Professional Nurse, No. 8, 399-401, May 1989.

Moore, K., "Intermittent self-catheterisation research-based practice," British Journal of Nursing, Vol. 4, No. 18, 1057-8, 1060, 1062-3, 1995.

Oldbury, M., "Hard won comfort... self-catheterisation," Nursing Times, Vol. 88, No. 13, 86, March 1992.

Oliver, H., "The treatment of choice... intermittent self-catheterisation," Nursing Times, Vol. 84, No. 31, 70, Aug. 1988.

UNITED STATES PATENT AND TRADEMARK OFFICE
CERTIFICATE OF CORRECTION

PATENT NO. : 6,736,805 B2
DATED : May 18, 2004
INVENTOR(S) : Anette Israelsson et al.

It is certified that error appears in the above-identified patent and that said Letters Patent is hereby corrected as shown below:

OTHER PUBLICATIONS, cont'd.,

Perkash, I. et al., "Clean intermittent catheterisation in spinal cord injured patients: a follow up study," J. Urol, Vol. 149, 1068-1071, 1993.

Perrouin-Verbe, B. et al., "Clean intermittent catheterisation from the acute period in spinal cord injury patients. Long term evaluation of urethral and genital tolerance," Paraplegia, No. 33, 619-624, 1995.

Rainville, N., "The current nursing procedure for intermittent urinary catheterization in rehabilitation facilities," Rehabilitation Nursing, Vol. 19, No. 6, 330-3, 382, Nov.-Dec. 1994.

Sibley, L., "Confidence with incontinence," Nursing Times, Vol. 84, No. 46, 42-43, Nov. 1988.

Vaidyanathian, S. et al., "Urethral cytology in spinal cord injury patients performing intermittent catheterisation," Paraplegia, No. 32, 493-500, 1994.

Waller, L. et al., "Clean intermittent catheterisation in spinal cord injury patients: long term followup of a hydrophilic low friction technique," J.Urol, Vol. 153, No. 2, 345-348, February 1995.

Webb, R. et al., "Clean intermittent self-catheterisation in 172 adults," Br. J Urol, Vol. 65, 20-23, 1990.

Willis, J., "Intermittent catheters," Professional Nurse, Vol. 10, No. 8, 523-524, May 1995.

Winder, A., "Intermittent self-catheterisation," Nursing Times, Vol. 86, No. 43, 63-4, Oct. 1990.

Winder, A., "Achieving independence... self-catheterisation," Nursing Times, Vol. 90, No. 22, 50-51, June 1994.

UNITED STATES PATENT AND TRADEMARK OFFICE
CERTIFICATE OF CORRECTION

PATENT NO.    : 6,736,805 B2
DATED         : May 18, 2004
INVENTOR(S)   : Anette Israelsson et al.

It is certified that error appears in the above-identified patent and that said Letters Patent is hereby corrected as shown below:

OTHER PUBLICATIONS, cont'd.,

```
    Wyndaele, J. et al., "Clean Intermittent self-
  catheterisation: a 12 year follow up," J.Urol, Vol. 143,
  906-908, Nov. 1989.
```

Column 1,
Line 4, after "37" should be inserted -- C.F.R. §1.53(d) --.

Column 2,
Line 43, after "OF" should be inserted -- THE --.

Column 6,
Line 49, "thereof" should be -- thereof. --.

Column 7,
Line 36, "thereof" should be -- thereof. --.

Signed and Sealed this

Sixteenth Day of August, 2005

JON W. DUDAS
*Director of the United States Patent and Trademark Office*